United States Patent
Cao et al.

(10) Patent No.: US 11,684,375 B2
(45) Date of Patent: Jun. 27, 2023

(54) ULTRASONIC OSTEOTOME BIT

(71) Applicant: BEIJING SMTP TECHNOLOGY CO., LTD., Beijing (CN)

(72) Inventors: Qun Cao, Beijing (CN); Xiaoming Hu, Beijing (CN); Chunyuan Li, Beijing (CN)

(73) Assignee: BEIJING SMTP TECHNOLOGY CO., LTD., Beijing (CN)

( * ) Notice: Subject to any disclaimer, the term of this patent is extended or adjusted under 35 U.S.C. 154(b) by 302 days.

(21) Appl. No.: 16/651,950

(22) PCT Filed: Aug. 12, 2018

(86) PCT No.: PCT/CN2018/100140
§ 371 (c)(1),
(2) Date: Mar. 27, 2020

(87) PCT Pub. No.: WO2019/062348
PCT Pub. Date: Apr. 4, 2019

(65) Prior Publication Data
US 2020/0305892 A1    Oct. 1, 2020

(30) Foreign Application Priority Data
Sep. 29, 2017  (CN) .......................... 201710908425.6

(51) Int. Cl.
*A61B 17/16* (2006.01)
(52) U.S. Cl.
CPC ...... *A61B 17/1615* (2013.01); *A61B 17/1644* (2013.01); *A61B 2017/1651* (2013.01)

(58) Field of Classification Search
CPC ....................................... A61B 17/16–17/1697
See application file for complete search history.

(56) References Cited

U.S. PATENT DOCUMENTS

| | | | |
|---|---|---|---|
| 5,632,745 A * | 5/1997 | Schwartz | ............... A61L 27/58 606/77 |
| 6,283,981 B1 * | 9/2001 | Beaupre | ......... A61B 17/320068 606/169 |

(Continued)

FOREIGN PATENT DOCUMENTS

| CN | 102143715 A | 8/2011 |
|---|---|---|
| CN | 104066389 A | 9/2014 |

(Continued)

*Primary Examiner* — Zade Coley
(74) *Attorney, Agent, or Firm* — Seed IP Law Group LLP

(57) ABSTRACT

An ultrasonic osteotome bit, comprising a bit body (1), a bit bar (2) and a bit tip (3). One end of the bit bar (2) is connected to the bit tip (3), and the other end of the bit bar (2) is connected to the bit body (1). The bit tip (3) is of a prism or substantially prism structure with the cross section of a polygonal structure, and the bit tip (2) has at least two cutting faces of different cutting widths. The bit is provided with a liquid flow hole (41), and the bit tip (3) is provided with a knurled structure that extends from a foremost end face of the bit tip (3) towards the bit bar (2) to form a file-type bit. The ultrasonic osteotome bit not only meets the requirement of a surgeon for the accuracy of bone cutting width, but also saves the time required to replace bits of different widths, thereby improving the surgical efficiency.

18 Claims, 3 Drawing Sheets

(56) References Cited

U.S. PATENT DOCUMENTS

| | | | |
|---|---|---|---|
| 6,423,082 B1 * | 7/2002 | Houser | A61B 17/320068 606/169 |
| 6,491,708 B2 * | 12/2002 | Madan | A61B 17/320068 310/334 |
| 8,075,564 B2 * | 12/2011 | Lee | A61C 8/0092 433/144 |
| 8,142,461 B2 * | 3/2012 | Houser | A61B 17/320092 606/169 |
| 8,348,967 B2 | 1/2013 | Stulen | |
| 9,387,004 B2 * | 7/2016 | Young | A61B 17/32002 |
| 10,327,827 B2 | 6/2019 | Young et al. | |
| 2002/0103497 A1 * | 8/2002 | Satou | A61B 17/320068 606/169 |
| 2002/0156493 A1 | 10/2002 | Houser et al. | |
| 2003/0204199 A1 * | 10/2003 | Novak | A61B 17/320068 606/169 |
| 2008/0188878 A1 * | 8/2008 | Young | A61B 17/1628 606/171 |
| 2008/0234708 A1 * | 9/2008 | Houser | A61B 17/320068 606/169 |
| 2009/0143795 A1 | 6/2009 | Robertson | |
| 2013/0123774 A1 | 5/2013 | Zadeh | |
| 2013/0226189 A1 * | 8/2013 | Young | A61F 2/4607 606/99 |
| 2014/0276721 A1 * | 9/2014 | Arthur | A61B 18/042 606/85 |
| 2014/0276849 A1 * | 9/2014 | Voic | A61B 17/320068 606/83 |
| 2014/0316415 A1 * | 10/2014 | Young | A61B 17/1637 606/84 |
| 2016/0374706 A1 | 12/2016 | Cotter et al. | |
| 2017/0119404 A1 * | 5/2017 | Ueda | A61B 17/1675 |
| 2019/0110799 A1 * | 4/2019 | Sun | A61B 17/1628 |
| 2019/0239917 A1 * | 8/2019 | Sawada | A61B 17/16 |
| 2019/0247069 A1 * | 8/2019 | Fujisaki | A61B 17/16 |

FOREIGN PATENT DOCUMENTS

| | | |
|---|---|---|
| CN | 104066392 A | 9/2014 |
| CN | 107582128 A | 1/2018 |
| EP | 0 456 470 A1 | 11/1991 |
| EP | 2 135 569 A2 | 12/2009 |
| WO | 2006/059120 A1 | 6/2006 |
| WO | 2017/027745 A1 | 2/2017 |
| WO | 2017/027853 A1 | 2/2017 |

* cited by examiner

ULTRASONIC OSTEOTOME BIT

TECHNICAL FIELD

The present disclosure belongs to the field of surgical instruments, and in particular to an ultrasonic osteotome bit.

BACKGROUND ART

In an orthopedic ultrasound operation, a surgeon uses an ultrasonic osteotome to perform cutting, grinding or shaping on bones or other biological tissue and bionic tissues thereof (such as cartilages and bone cement).

In the existing ultrasonic osteotome, a tip portion, i.e., a bit tip, only has a single cutting width, such that when the surgeon needs to perform accurate large-width cutting, it can only be done by means of multiple reciprocating cutting or by replacing ultrasonic scalpel bits of different widths. It is difficult for the surgeon to accurately achieve the width of an incision due to reciprocating cutting, and the replacement of the ultrasonic scalpel bits with different widths takes a relatively long time, thus affecting the continuity of surgical operation by the surgeon and extending the time of operation to a certain extent.

SUMMARY

According to the present disclosure, an ultrasonic osteotome bit is designed, which solves the problem in the prior art of unsatisfactory effects in use due to the tip portion, i.e., the bit tip, of the ultrasonic osteotome only having a single cutting width.

In order to solve the above technical problem, the present disclosure provides an ultrasonic osteotome bit, comprising a bit bar, a bit body and a bit tip. One end of the bit bar is connected to the bit tip, and the other end of the bit bar is connected to the bit body. The bit tip is of a prism or substantially prism structure with a cross section of a polygonal structure, and the bit tip has at least two cutting faces with different cutting widths.

In the ultrasonic osteotome bit of the present disclosure, preferably, the polygonal structure is of a centrosymmetric structure, with all internal angles formed by adjacent sides of the polygonal structure being an obtuse angle.

In the ultrasonic osteotome bit of the present disclosure, preferably, the shortest distance among the distances between respective opposite sides of the polygonal structure is not equal to the longest distance among the distances between respective opposite sides of the polygonal structure, and the two opposite sides having the shortest distance are perpendicular to the two opposite sides having the longest distance, so that the bit tip has at least two accurate and easy-to-operate cutting widths.

In the ultrasonic osteotome bit of the present disclosure, preferably, the bit is provided with a liquid flow hole.

In the ultrasonic osteotome bit of the present disclosure, preferably, the liquid flow hole comprises a longitudinal central hole of the bit body and a drainage hole penetrating the tail end of the longitudinal central hole of the bit body, and the tail end of the longitudinal central hole of the bit body is located at a connecting end, connected to the bit bar, of the bit body.

In the ultrasonic osteotome bit of the present disclosure, preferably, the drainage hole vertically penetrates a tail end of the longitudinal central hole of the bit body.

In the ultrasonic osteotome bit of the present disclosure, preferably, the liquid flow hole comprises a longitudinal central through hole that penetrates the bit body and the bit bar and extends to the bit tip.

In the ultrasonic osteotome bit of the present disclosure, preferably, the bit tip is provided with a knurled structure that extends from a foremost end face of the bit tip towards the bit bar to form a file-type bit.

In the ultrasonic osteotome bit of the present disclosure, preferably, in the bit tip, the length of the knurled structure, on the cutting face with the minimum cutting width, extending towards the bit bar is greater than the length of the knurled structure, on the cutting face with the maximum cutting width, extending towards the bit bar.

In the ultrasonic osteotome bit of the present disclosure, preferably, the foremost end face of the bit tip is of a convex structure or a concave structure.

In the ultrasonic osteotome bit of the present disclosure, preferably, the bit bar is in transitional connection with the bit body through a bevel, the bit bar is in smooth transition with the bit tip, and the tail end of the bit body is provided with a threaded structure to connect with an ultrasonic device.

The ultrasonic osteotome bit has the beneficial effects as follows.

(1) The present disclosure solves the problem in the prior art of unsatisfactory effects in use due to the tip portion of the ultrasonic osteotome only having a single cutting width. It is particularly suitable for achieving accurate cutting on bone tissues or other biological tissues (such as cartilages) and their bionic tissues (such as bone cement) by means of ultrasonic vibration.

(2) The present disclosure not only meets the requirement of a surgeon for the accuracy of bone cutting width, but also saves the time required to replace bits of different widths, thereby improving the surgical efficiency.

(3) The present disclosure has a simple structure and long service life, is convenient for adjusting the cutting width of the bit, is easy to operate, and has wide adjustable range.

(4) In the present disclosure, a hollow liquid flow hole is machined inside the bit, the bit tip is machined into a file-type structure to reduce the contact area between the bit and the tissues during cutting and at the same time provide a flow path of a liquid flow to reduce the temperature of a cutting area. The hollow liquid flow hole inside the bit can also drain the debris of tissue cutting through the inner hole under negative pressure.

REFERENCE NUMERALS

1—bit body; 11—connecting thread; 2—bit bar; 3—bit tip; 31—foremost end face; 4—liquid flow hole; 41—drainage hole.

DETAILED DESCRIPTION OF THE EMBODIMENTS

The technical solution of the present disclosure will be clearly and completely described below in conjunction with the accompanying drawings, and obviously, the described embodiments are part of, not all of, the embodiments of the present disclosure. All other embodiments obtained by those of ordinary skill in the art based on the embodiments of the present disclosure without any creative effort shall fall within the scope of protection of the present disclosure.

In the description of the present disclosure, it should be noted that the orientation or positional relationship indicated by the terms "center", "upper", "lower", "left", "right", "vertical" "horizontal", "inner", "outer", etc. are based on the orientation or positional relationship shown in the accompanying drawings and are intended to facilitate the description of the present disclosure and simplify the description only, rather than indicating or implying that the device or element referred to must have a particular orientation or be constructed and operated in a particular orientation, and will not to be interpreted as limiting the present disclosure. In addition, the terms "first", "second" and "third" are used for descriptive purposes only and should not be construed as indicating or implying relative importance.

In the description of the present disclosure, it should be noted that the terms "mounting", "connecting" and "connection" should be understood in a broad sense, and unless otherwise explicitly specified or defined, for example, it may be a fixed connection, a detachable connection or an integrated connection; may be a mechanical connection or an electrical connection; and may be a direct connection or an indirect connection through an intermediate medium, or may be a communication between the interior of two elements. For those of ordinary skill in the art, the specific meanings of the terms mentioned above in the present disclosure should be construed according to specific circumstances.

Figure 1:
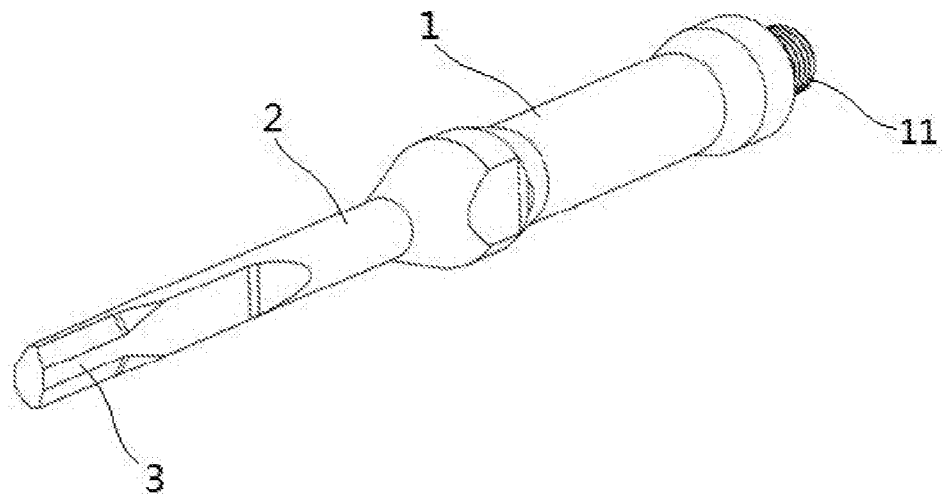
FIG. 1 is a first operating state view of an ultrasonic osteotome bit according to a first embodiment of the present disclosure.
Figure 2:
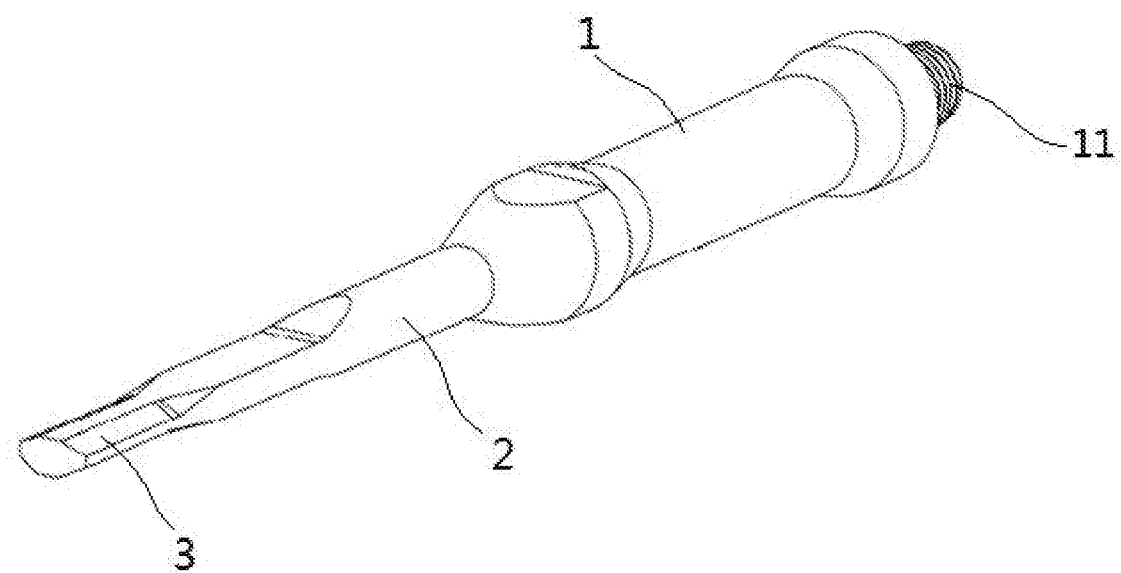
FIG. 2 is a second operating state view of the ultrasonic osteotome bit according to the first embodiment of the present disclosure.
Figure 3:
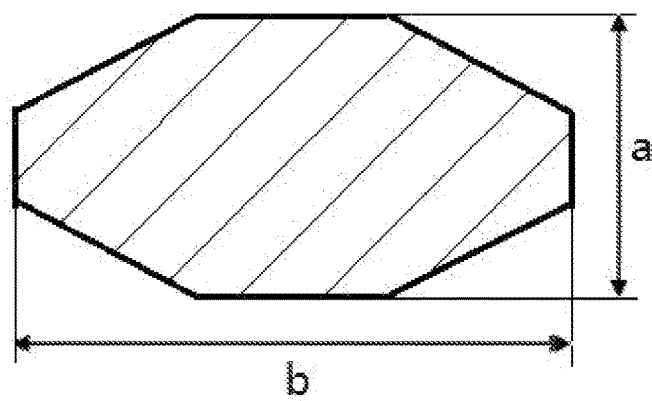
FIG. 3 is a cross-sectional view of a bit tip of the ultrasonic osteotome bit according to the first embodiment of the present disclosure.

The present disclosure will be further described in detail below by specific embodiments and with reference to the accompanying drawings. FIGS. 1 to 3 show an ultrasonic osteotome bit according to a first embodiment of the present disclosure. FIG. 1 is a first operating state view of an ultrasonic osteotome bit according to this embodiment, and FIG. 2 is a second operating state view of the ultrasonic osteotome bit according to this embodiment. As shown in FIGS. 1 and 2, the ultrasonic osteotome bit according to the first embodiment of the present disclosure comprises a bit body 1, a bit bar 2 and a bit tip 3, with one end of the bit bar 2 being connected to the bit tip 3, and the other end of the bit bar 2 being connected to the bit body 1. The bit tip 3 is of a prism or substantially prism structure with the cross section of a polygonal structure, and the bit tip 3 has at least two cutting faces with different cutting widths to be in contact with a biological tissue, such as a bone. During operation, the cutting faces of the bit tip 3 may be selected by rotating the operating angle of the bit, thereby obtaining at least two different cutting widths. In this embodiment, a prism face, or a lateral face of a substantially prism structure, of the bit tip 3 constitutes at least two cutting faces with different cutting widths.

FIG. 3 is a cross-sectional view of the bit tip of the ultrasonic osteotome bit according to this embodiment. As shown in FIG. 3, the bit tip 3 has the cross section of a polygonal structure. Preferably, the polygonal structure is a centrosymmetric structure, with all internal angles formed by adjacent sides of the polygonal structure being an obtuse angle. In this embodiment, the polygonal structure is of a convex octagonal structure. When the diameter of the bit is increased, more than two cutting widths can be achieved by increasing the number of cross-sectional sides.

As shown in FIG. 3, the shortest distance among the distances between respective opposite sides of the polygonal structure is not equal to the longest distance among the distances between respective opposite sides of the polygonal structure, and the two opposite sides having the shortest distance are perpendicular to the two opposite sides having the longest distance, so that the bit tip has at least two cutting widths, so that the bit can have at least two accurate cutting widths when axially rotating for cutting, and the two accurate cutting widths are easy to choose so as to facilitate operation.

FIGS. 1 and 2 show two typical operating states of the ultrasonic osteotome bit according to the first embodiment of the present disclosure. The ultrasonic osteotome bit in FIG. 2 is rotated by 90 degrees, relative to the ultrasonic osteotome bit in FIG. 1, along the axis of the bit to perform cutting. FIG. 3 is a cross-sectional view of the bit tip 3 perpendicular to the axis. When the ultrasonic osteotome bit is in the operating state shown in FIG. 1, its effective cutting width is represented by a in FIG. 3, and the effective cutting width is the shortest distance among the distances between respective opposite sides of the polygonal structure; and when the ultrasonic osteotome bit is in the operating state shown in FIG. 2, its effective cutting width is represented by b in FIG. 3, and the effective cutting width is the longest distance among the distances between respective opposite sides of the polygonal structure. As shown in FIG. 3, the effective cutting width a is not equal to the effective cutting width b, and the opposite sides having the effective cutting width a is perpendicular to the opposite sides having the effective cutting width b, so that the bit has two accurate cutting widths when axially rotating for cutting, and the accurate control of tissue cutting width can be achieved as long as the bit rotates 90 degrees. Of course, the ultrasonic osteotome bit may have any operating angle, and the cutting width of a biological tissue may be any value between the two accurate cutting widths. When the diameter of the bit is increased, more than two accurate cutting widths can be achieved by increasing the number of cross-sectional sides.

As shown in FIGS. 1 and 2, the tail end of the bit body 1 is provided with a threaded structure 11 to be connected to an ultrasonic device. In this embodiment, the tail end of the bit body 1 is connected to an ultrasonic amplitude transformer. The threaded structure 11 may be an external threaded structure or an internal threaded structure. In this embodiment, an external threaded structure is used. One end of the bit bar 2 is connected to the bit body 1, and the bit bar 2 is in transitional connection with the bit body 1 through a bevel. The other end of the bit bar 2 is connected to the bit tip 3, and the bit bar 2 is in transitional connection with the bit tip 3. The ultrasonic osteotome bit may be of a one-piece structure or a multi-piece assembly structure. In this embodiment, the ultrasonic osteotome bit uses a one-piece structure.

Figure 4:
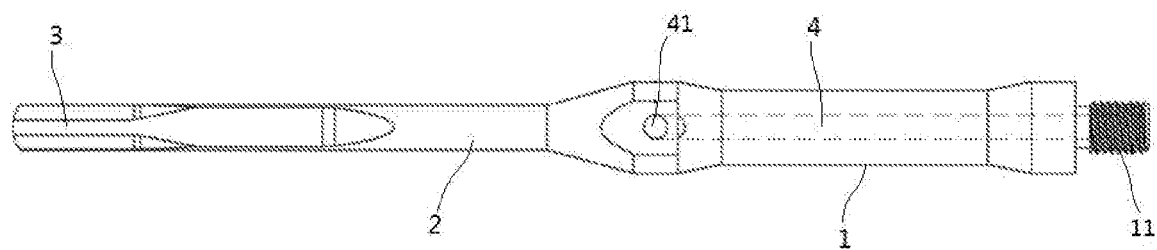
FIG. 4 is a first operating state view of an ultrasonic osteotome bit according to a second embodiment of the present disclosure.
Figure 5:
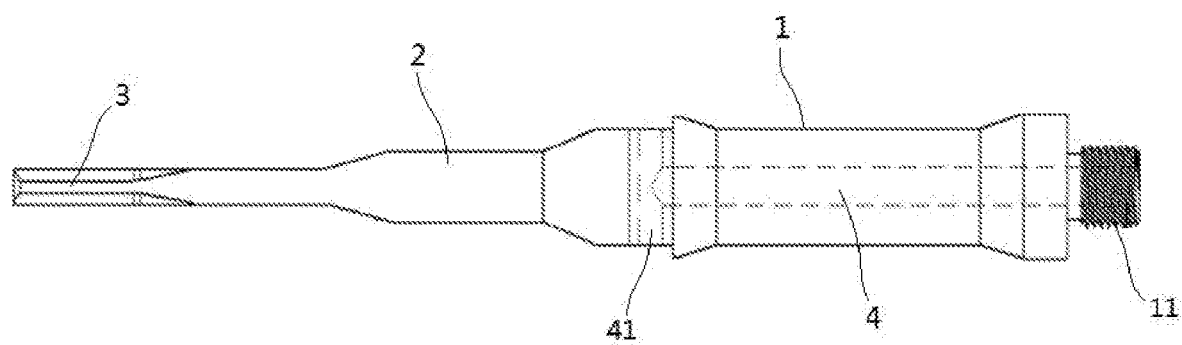
FIG. 5 is a second operating state view of the ultrasonic osteotome bit according to the second embodiment of the present disclosure.

FIGS. 4 and 5 show an ultrasonic osteotome bit according to a second embodiment of the present disclosure. FIG. 4 is a first operating state view of an ultrasonic osteotome bit according to a second embodiment of the present disclosure; FIG. 5 is a second operating state view of the ultrasonic osteotome bit according to the second embodiment of the present disclosure. As shown in FIGS. 4 and 5, the ultrasonic osteotome bit according to the second embodiment of the present disclosure has a structure substantially the same as the ultrasonic osteotome bit according to the first embodiment of the present disclosure, except that a liquid flow hole 4 is provided in the ultrasonic osteotome bit according to the second embodiment of the present disclosure. The liquid flow hole 4 comprises a longitudinal central hole of the bit body 1 and a drainage hole 41 penetrating the tail end of the longitudinal central hole of the bit body 1. The longitudinal drainage hole 41 transversely extends in a direction perpendicular to the axis of the bit body. The tail end of the longitudinal central hole of the bit body 1 is at a connecting end, connected to the bit bar 2, of the bit body 1. A liquid flow may be introduced into the bit bar 2 through the liquid flow hole 4 and flow to the bit tip 3 under gravity so as to reduce the temperature of a cutting area. In this embodiment, the drainage hole 41 vertically penetrates the tail end of the longitudinal central hole of the bit body 1.

Figure 6:
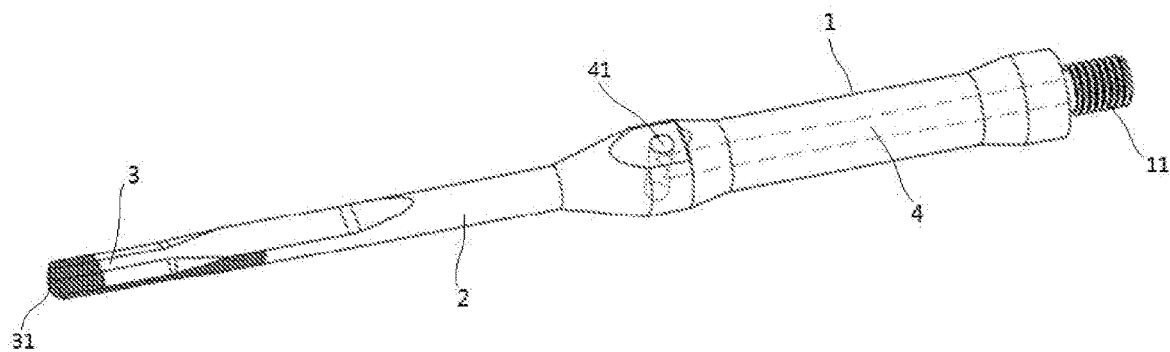
FIG. 6 is a schematic structural view of an ultrasonic osteotome bit according to a third embodiment of the present disclosure.

FIG. 6 is a schematic structural view of an ultrasonic osteotome bit according to a third embodiment of the present disclosure. As shown in FIG. 6, the ultrasonic osteotome bit according to the third embodiment of the present disclosure has a structure substantially the same as the ultrasonic osteotome bit according to the second embodiment of the present disclosure, except that the ultrasonic osteotome bit in the third embodiment of the present disclosure is provided, at the bit tip 3, with a knurled structure that extends from a foremost end face 31 of the bit tip 3 to the bit bar 2 to form a file-type bit. The knurled structure can reduce the contact area between the ultrasonic osteotome and bone tissues, which increase the ultrasonic power density of the tissue surface and is also beneficial to allow the knurled structure to provide a liquid flow path to drain liquid to a surface of the cut tissue for cooling. The foremost end face 31 of the bit tip 3 is machined into a convex structure.

As shown in FIG. 6, in the ultrasonic osteotome bit according to the third embodiment of the present disclosure, in the bit tip 3, the length of the knurled structure, on the cutting face with the minimum cutting width, extending towards the bit bar 2 is greater than the length of the knurled structure, on the cutting face with the maximum cutting width, extending towards the bit bar 2.

Figure 7:
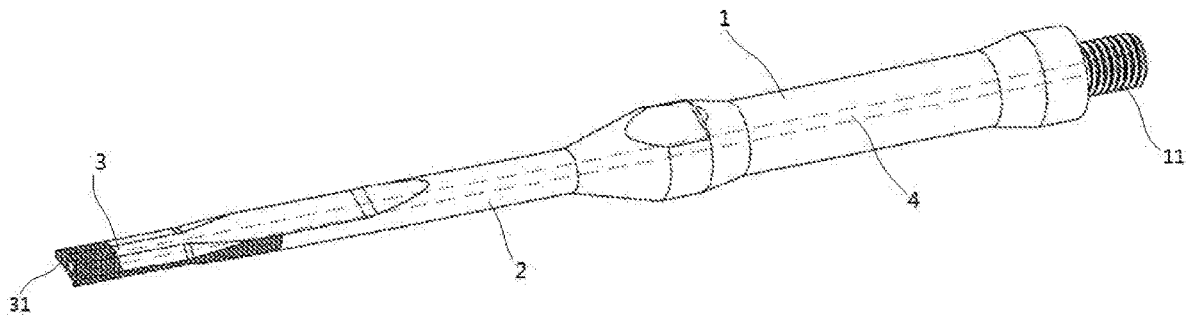
FIG. 7 is a schematic structural view of an ultrasonic osteotome bit according to a fourth embodiment of the present disclosure.

FIG. 7 is a schematic structural view of an ultrasonic osteotome bit according to a fourth embodiment of the present disclosure. As shown in FIG. 7, the ultrasonic osteotome bit according to the fourth embodiment of the present disclosure has a structure substantially the same as the ultrasonic osteotome bit according to the third embodiment of the present disclosure, except that in the ultrasonic osteotome bit in the fourth embodiment of the present disclosure, the liquid flow hole 4 penetrates the bit body 1 and the bit bar 2 and extends to the longitudinal central through hole of the bit tip 3. With such a design, a cooling liquid can be drained to reduce the temperature of the cutting area, and the debris of tissue cutting can be drawn out of the liquid flow hole under negative pressure so as to ensure the clear view of the surgical field. The foremost end face 31 of the bit tip 3 is machined into a concave structure.

The ultrasonic osteotome bit of the present disclosure can perform accurate cutting in multiple widths, which not only meets the requirement of a surgeon for the accuracy of bone cutting width, but also saves the time required to replace bits of different widths, thereby improving the surgical efficiency. The present disclosure has a simple structure and long service life, is convenient for adjusting the cutting width of the bit, is easy to operate, and has wide adjustable range.

Finally, it should be noted that the above various embodiments are merely used for illustrating rather than limiting the technical solutions of the present disclosure. Although the present disclosure has been described in detail with reference to the above various embodiments, those of ordinary skill in the art should understood that the technical solutions specified in the above various embodiments can still be modified, or some or all of the technical features therein can be equivalently substituted; and such modifications or substitutions do not make the essence of the corresponding technical solutions depart from the scope of the technical solutions of the various embodiments of the present disclosure.

The invention claimed is:

1. An ultrasonic osteotome bit for cutting bones, comprising a bit bar, a bit body and a bit tip, with a first end of the bit bar being connected to the bit tip, and a second end of the bit bar being connected to the bit body, wherein:
   the bit tip is of a straight prism or substantially straight prism shape with a cross section of a polygonal shape, and
   the bit tip has at least two cutting faces with different cutting widths, which are formed by at least one side face of the straight prism or substantially straight prism shape and through which the ultrasonic osteotome bit is operable to generate at least two incisions of different widths in a cutting object, wherein the at least two cutting faces extend from a foremost end face of the bit tip towards the bit bar, and wherein a shortest distance among distances between respective opposite sides of the polygonal shape is not equal to a longest distance among distances between respective opposite sides of the polygonal shape, and the two opposite sides having the shortest distance are perpendicular to the two opposite sides having the longest distance so that the bit tip has at least two cutting widths.

2. The ultrasonic osteotome bit according to claim 1, wherein
   the polygonal shape is centrosymmetric, with all internal angles formed by adjacent sides of the polygonal shape being obtuse angles.

3. The ultrasonic osteotome bit according to claim 1, wherein
   a first cutting width of the at least two cutting widths is equal to the shortest distance, and a second cutting width of the at least two cutting widths is equal to the longest distance.

4. The ultrasonic osteotome bit according to claim 3, wherein:
   the ultrasonic osteotome bit has at least two operating angles around its axis;
   the Ultrasonic osteotome bit has a first cutting width at a first operating angle of the at least two operating angles and a second cutting width at a second operating angle of the at least two operating angles; and
   the second operating angle is offset relative to the first operating angle by 90 degrees.

5. The ultrasonic osteotome bit according to claim 4, wherein the ultrasonic osteotome bit has a third operating angle, wherein the third operating angle is offset relative to the first operating angle by an angle of greater than 90 degrees or smaller than 90 degrees.

6. The ultrasonic osteotome bit according to claim 1, wherein
the bit is provided with a liquid flow hole.

7. The Ultrasonic osteotome bit according to claim 6, wherein
the liquid flow hole comprises a longitudinal central hole of the bit body and a drainage hole penetrating a tail end of the longitudinal central hole of the bit body, and the tail end of the longitudinal central hole of the bit body is located at a connecting end connected to the bit bar of the bit body.

8. The ultrasonic osteotome bit according to claim 6, wherein
the liquid flow hole comprises a longitudinal central through hole that penetrates the bit bar and the bit body and extends to the bit tip.

9. The ultrasonic osteotome bit according to claim 1, wherein
the bit tip is provided with a knurled structure that extends from a foremost end face of the bit tip towards the bit bar to form a file-type bit.

10. The ultrasonic osteotome bit according to claim 9, wherein
in the bit tip, a first length of the knurled structure, on a first cutting face with a minimum cutting width, extending towards the bit bar is greater than a second length of the knurled structure, on a second cutting face with a maximum cutting width, extending towards the bit bar.

11. The ultrasonic osteotome bit according to claim 1, wherein
a foremost end face of the bit tip is of a convex shape or a concave shape.

12. The ultrasonic osteotome bit according to claim 1, wherein
the bit bar is in transitional connection with the bit body through a bevel, the bit bar is in smooth transition with the bit tip, and a tail end of the bit body is provided with a threaded structure to connect with an ultrasonic device.

13. The ultrasonic osteotome bit according to claim 1, wherein:
the ultrasonic osteotome bit has at least two operating angles around its axis, and
the bit tip has a corresponding cutting face at each of the at least two operating angles.

14. The ultrasonic osteotome bit according to claim 1, wherein
the ultrasonic osteotome bit is formed as one-piece.

15. The ultrasonic osteotome bit according to claim 1, wherein
the cross-section of the bit tip is convex octagon.

16. The ultrasonic osteotome bit, according to claim 15, wherein
the opposite sides of the convex octagon are parallel with one another.

17. An operation method for an ultrasonic osteotome bit, the ultrasonic osteotome bit comprising a bit bar, a bit body and a bit tip, with one end of the bit bar being connected to the bit tip, and the other end of the bit bar being connected to the bit body, wherein the bit tip is of a straight prism or substantially straight prism shape with a cross section of a polygonal shape, the bit tip having at least two cutting faces with different cutting widths, which are formed by at least one side face of the straight prism or substantially straight prism structure and through which the ultrasonic osteotome bit is operable to generate at least two incisions of different widths in a cutting object, wherein the at least two cutting faces extend from a foremost end face of the bit tip towards the bit bar, the operation method comprising:
rotating the ultrasonic osteotome bit around as axis of the ultrasonic osteotome bit such that the ultrasonic osteotome bit performs cutting bones with one of the at least two cutting faces,
wherein a shortest distance among distances between respective opposite sides of the polygonal shape is not equal to a longest distance among distances between respective opposite sides of the polygonal shape, and the two opposite sides having the shortest distance are perpendicular to the two opposite sides having the longest distance so that the bit tip has at least two cutting widths.

18. An ultrasonic osteotome bit for cutting bones, comprising a bit bar, a bit body and a bit tip, with a first end of the bit bar being connected to the bit tip, and a second end of the bit bar being connected to the bit body, wherein:
the bit tip is of a straight prism or substantially straight prism shape with a cross section convex octagon,
the bit tip has at least two cutting faces with different cutting widths extending from a foremost end face of the bit tip to the bit bar,
a shortest distance among distances between respective opposite sides of the convex octagon is not equal to a longest distance among distances between respective opposite sides of the convex octagon, and the two opposite sides having the shortest distance are perpendicular to the two opposite sides having the longest distance, and
a first cutting width of the at least two cutting widths is equal to the shortest distance, and a second cutting width of the at least two cutting widths is equal to the longest distance.

\* \* \* \* \*

UNITED STATES PATENT AND TRADEMARK OFFICE
CERTIFICATE OF CORRECTION

PATENT NO.        : 11,684,375 B2
APPLICATION NO.   : 16/651950
DATED             : June 27, 2023
INVENTOR(S)       : Qun Cao et al.

Page 1 of 1

It is certified that error appears in the above-identified patent and that said Letters Patent is hereby corrected as shown below:

In the Claims

Column 8, Claim 15, Line 4:
"osteotome bit, according"
Should read:
--osteotome bit according--.

Column 8, Claim 17, Line 21:
"bit around as axis of"
Should read:
--bit around an axis of--.

Column 8, Claim 18, Line 38:
"with a cross section convex octagon,"
Should read:
--with a cross section of convex octagon,--.

Signed and Sealed this
First Day of April, 2025

Coke Morgan Stewart
*Acting Director of the United States Patent and Trademark Office*